United States Patent [19]

Fu et al.

[11] Patent Number: 5,414,011
[45] Date of Patent: * May 9, 1995

[54] PRESERVATIVE SYSTEM FOR OPHTHALMIC FORMULATIONS

[75] Inventors: Cherng-Chyi R. Fu, Saratoga; Deborah M. Lidgate, Los Altos, both of Calif.

[73] Assignee: Syntex (U.S.A.) Inc., Palo Alto, Calif.

[*] Notice: The portion of the term of this patent subsequent to May 5, 2009 has been disclaimed.

[21] Appl. No.: 329,451

[22] Filed: Mar. 28, 1989

Related U.S. Application Data

[63] Continuation-in-part of Ser. No. 96,173, Sep. 11, 1987, abandoned.

[51] Int. Cl.$^6$ .................. A61K 31/47; A61K 31/14
[52] U.S. Cl. ..................... 514/413; 514/643; 514/912; 514/914
[58] Field of Search ............. 514/413, 912, 914, 643

[56] References Cited

U.S. PATENT DOCUMENTS

| | | | |
|---|---|---|---|
| 4,087,538 | 5/1978 | Portnoff | 514/914 |
| 4,087,539 | 5/1978 | Muchowski et al. | 424/274 |
| 4,089,969 | 5/1978 | Muchowski et al. | 424/274 |
| 4,097,579 | 6/1978 | Muchowski et al. | 424/274 |
| 4,230,724 | 10/1980 | Cooper et al. | 514/912 |
| 4,232,038 | 11/1980 | Kluge et al. | 424/274 |
| 4,336,151 | 6/1982 | Like et al. | 252/106 |
| 4,336,152 | 6/1982 | Like et al. | 252/106 |
| 4,349,563 | 9/1982 | Gilbert et al. | 514/914 |
| 4,454,157 | 6/1984 | Waterbury | 424/274 |
| 4,474,751 | 10/1984 | Haslan et al. | 514/912 |
| 4,474,811 | 10/1984 | Masuda et al. | 514/912 |
| 4,500,538 | 2/1985 | Waltersdorf | 514/367 |
| 4,559,343 | 12/1985 | Han et al. | 514/264 |
| 4,607,038 | 8/1986 | Ogata et al. | 514/291 |

FOREIGN PATENT DOCUMENTS 23318 2/1985 Japan.

OTHER PUBLICATIONS

Chem Abst 103:115887g (1985). Mahoney et al.
The Condensed Chemical Dictionary, Seventh Ed., Reinhold Publishing Co., N.Y., p. 985.
McCutcheon's "Emulsifiers and detergents" North American Ed., 1983 p. 154.
Schmolka, Irving R. J. Soc. Cosmet. Chem. 24, 577-592 (Aug. 9, 1973).
"Influence of (Ethoxy)$_5$ Octyl Phenol on the Antibacterial Properties of Preservatives", M. T. Nadir, et al., Journal of Pharmacy and Pharmacology, vol. 29, Supplement, Dec. 1977, p. 67P.
"Ocufen (flurbioprofen sodium) 0.03% Liquifilm steril ophthalmic solution," Allergan, product description sheet, one page.
Remington's Pharmaceutical Sciences, 15th Ed., pp. 1489-1504, (1975).

*Primary Examiner*—Zohreh Fay
*Attorney, Agent, or Firm*—Derek P. Freyberg

[57] ABSTRACT

Stable, clear, antimicrobially effective, ophthalmic formulations are disclosed which provide an antimicrobially effective preservative. The formulations include an ophthalmologically effective amount of a drug, which is a —COOH group-containing non-steroidal anti-inflammatory drug (NSAID) alone or in combination with an antibiotic drug, and a preservative system formed of a quaternary ammonium preservative and a nonionic polyoxyethylated octylphenol surfactant, all in an aqueous vehicle. The preservative system can be used with other formulations which require the preservative to be ophthamologically acceptable and antimicrobially effective. These formulations are useful for treating diseases and/or conditions that are either caused by, associated with or accompanied by inflammatory processes, including, among others, glaucoma, cystoid macular edema, uveitis, diabetic retinopathy and conjunctivitis, or any trauma caused by eye surgery or eye injury. When the formulation is further comprised of an ophthalmologically acceptable antibiotic, the antibiotic is preferably tobramycin which has been found not to interfere with the rate of diffusion of the NSAID. The combination of the NSAID and antibiotic is particularly effective in simultaneously preventing and/or eliminating infection while preventing and/or eliminating inflammation.

10 Claims, No Drawings

5,414,011

PRESERVATIVE SYSTEM FOR OPHTHALMIC FORMULATIONS

CROSS REFERENCES

This application is a continuation-in-part of our earlier filed, application Ser. No. 07/096,173 filed Sep. 11, 1987, now abandoned, which application is incorporated herein by reference and to which application Applicants hereby claim priority under 35 USC §120.

FIELD OF THE INVENTION

The present invention relates to improved ophthalmic formulations, particularly to ophthalmic formulations which use an improved preservative system comprising a quaternary ammonium preservative and a stabilizing amount of a nonionic polyoxyethylated octylphenol surfactant for ophthalmic formulations of carboxyl ("—COOH") group-containing non-steroidal anti-inflammatory drugs ("NSAIDs").

The formulations may also contain an opthalmologically acceptable antibiotic, preferably tobramycin. The invention also relates to methods of using these formulations for treating diseases and/or conditions that are either caused by, associated with or accompanied by inflammatory processes, including, among others, glaucoma, cystoid macular edema, uveitis, diabetic retinopathy and conjunctivitis, or any trauma caused by eye surgery or eye injury. In addition, the formulation can be used to treat bacterial infection.

BACKGROUND OF THE INVENTION

To be ophthalmologically acceptable, a formulation must process a number of characteristics to comply with the general FDA requirements of being safe and effective. In that eyes are quite sensitive to pain, the formulation must be developed such that it causes little to no discomfort or stinging when administered. This feature is particularly important to insure user complaince and important in that such formulations are often administered in order to relieve pain or inflammation. The ophthalmic use of NSAID compounds was disclosed in U.S. Pat. No. 4,454,151, where NSAID compounds (such as those described in U.S. Pat. Nos. 4,089,969; 4,232,038; 4,087,539 and 4,097,579) were exemplified in formulation with $NaH_2PO_4.H_2O$, $Na_2HPO_4.H_2O$, NaCl, benzalkonium chloride ("BAC") and sterilized water. While the formulations described in the '151 patent were efficacious, a complex was found to form between the NSAID and the BAC.

Due to the formation of this complex, the formulations did not have the stability desired for shelf life in commercial applications. A reasonable minimum shelf life is at least about one year, representing sufficient time to package, ship, and store a formulation without having to replace expired stock too frequently.

An ophthalmic suspension containing a particular NSAID is disclosed in U.S. Pat. No. 4,087,538 issued May 2, 1978. The suspension is aqueous based and can include benzalkonium chloride. Another ophthalmic formulation is disclosed in U.S. Pat. No. 4,559,343 issued Dec. 17, 1985. The formulation is aqueous based and includes an NSAID and a benzalkonium chloride preservative. A somewhat similar ophthalmic formulation is disclosed in U.S. Pat. No. 4,607,038 issued Aug. 19, 1986. This formulation includes a specific NSAID (pranoprofen) in an aqueous based formula with a known preservative. U.S. Pat. No. 4,474,751 issued Oct. 2, 1984 discloses ophthalmic formulations which gel in the eye in order to increase the bioavailability of the drug. The '751 patent discloses a large number of different active ingredients and excipient material. When this disclosure is taken in view of the other patents discussed above and the publications cited in each of them, the vast number of different ways of creating an ophthalmic formulation becomes apparent. Although there may be a considerable number of possible formulations and variations thereof, only certain specific formulations will meet all the requirements for being ophthalmologically acceptable.

In general, an ophthalmic formulation contains an active compound and various ophthalmologically acceptable excipients, in the form of a solution, an ointment, a suspension, etc. In order for an excipient to be ophthalmologically acceptable, it must be non-irritating to the eye in combination with other excipients and an active ingredient. The excipients must not prevent the active ingredient from penetrating the blood-aqueous barrier and/or difusing through the various ocular substructures to the site where it is pharmacologically active. The excipients can interact with each other or the active drug. Accordingly, care in formulating is required in that so many materials may be used. These materials generally include a tonicifier, a preservative, a surfactant, a buffering system, a chelating agent, a viscosity agent as well as other stabilizing agents. Ophthalmic formulations must be sterile and must be preserved with an effective anti-microbial agent.

Organo-mercurials (e.g., thimerosal, phenylmercuric acetate and phenylmercuric nitrate) have been used extensively as the preservative in ophthalmic solutions. These compounds, however, pose difficulties due to potential mercury toxicity as well as poor chemical stability. Benzalkonium chloride, a quaternary ammonium compound, has been widely used in ophthalmic solutions, and is considered to be the preservative of choice. However, BAC has typically been considered to be incompatible with anionic drugs (e.g., salicylates or nitrates, etc.) and can be inactivated by surfactants.

Many NSAIDs such as ketorolac, indomethacin, flurbiprofen and suprofen) are being developed for ocular use because of their activity as anti-inflammatory agents as well as their ability to prevent cystoid macular edema.

These NSAIDs have proven to be incompatible with quaternary ammonium compounds such as BAC because they can form a complex with them, rendering the preservative less available to serve its function, as is the case with other ophthalmic drugs that contain a —COOH group. Thus, less preferred preservatives have been used in such ophthalmic formulations. For example, Ocufen Ophthalmic solution, the first NSAID (flurbiprofen) approved by the FDA for ophthalmic use, incorporates thimerosal (with EDTA) as its preservative system.

A need has continued to exist for a stable, clear, antimicrobial preservative effective ophthalmic formulation for NSAIDs alone or with antibiotics using BAC as the preservative, and an improved preservative system for —COOH group containing ophthalmic drugs.

SUMMARY OF THE INVENTION

A primary object of the invention is to describe and disclose a formulation containing an ophthalmologically effective amount of an NSAID alone or in combination with an antibiotic, a quaternary ammonium preservative and a stabilizing amount of a nonionic polyoxyethylated octylphenol surfactant, all in an aqueous vehicle.

Another object of the invention is to describe and disclose an antimicrobially effective preservative system for ophthalmic drugs having a —COOH group, including a quaternary ammonium preservative and a stabilizing amount of a nonionic surfactant.

A feature of the present invention is that it allows for the separation of a stable, i.e., clear and antimicrobially effective, NSAID-containing ophthalmic formulations without the need for an organo-mercurial preservative.

Another feature is that methods for treating ophthalmic diseases in mammals using the ophthalmic pharmaceutical formulations of the invention are provided.

An advantage of the present invention is that it is useful in the treatment of diseases or conditions associated with or accompanied by inflammatory processes, including, among others, glaucoma, cystoid macular edema, uveitis, diabetic retinopathy and conjunctivitis, or any trauma caused by eye surgery or eye injury.

These and other objects, advantages and features of the present invention will become apparent to those persons skilled in the art upon reading the details of the composition, manufacture and usage as more fully set forth below. Reference being made to the accompanying general structural formulae forming a part hereof wherein like symbols refer to like molecular moieties throughout.

DETAILED DESCRIPTION AND PREFERRED EMBODIMENTS

Before the present and processes for making and using such are disclosed and described, it is to be understood that this invention is not limited to the particular compositions, components or methods of use described as such compositions, components and methods may, of course, vary. It is also to be understood that the terminology used herein is for the purpose of describing particular embodiments only, and is not intended to be limiting since the scope of the present invention will be limited only by the appended claims.

It must be noted that as used in this specification and the appended claims, the singular forms "a", "a" and "the" include plural referents unless the context clearly dictates otherwise. Thus, for example, reference to "a pharmaceutically acceptable salt" includes mixtures of salts, references to "an NSAID" includes reference to mixtures of such NSAIDS, reference to "the method of administration" includes one or more different methods of administration known to those skilled in the art.

Definitions

As used herein, the term "NSAID" means an ophthalmologically acceptable carboxyl group containing non-steroidal anti-inflammatory drug.

As used herein, the term "q.s." means adding a quantity sufficient to achieve a stated function, e.g., to bring a solution to the desired volume (i.e., 100%).

As used herein, the term "treatment" or "treating" means any treatment of a disease and/or condition in a mammal, including:

(i) preventing the disease and/or condition, that is, causing the clinical symptoms of the disease not to develop;

(ii) inhibiting the disease and/or condition, that is, arresting the development of clinical symptoms; and/or (iii) relieving the disease and/or condition, that is, causing the regression of clinical symptoms.

As used herein, the term "effective amount" means a dosage sufficient to provide treatment for the disease state being treated. This will vary depending on the patient, the disease and the treatment being effected.

As used herein, the term "antimicrobially effective" refers to the stability of the formulation prior to administration and means ability to withstand the U.S. Pharmacopia antimicrobial challenge put by a panel of microbes.

As used herein, the term "stabilizing" means keeping a formulation clear and antimicrobially effective for its minimum reasonable shelf life, e.g., at least one year.

"Ketorolac tromethamine" shall mean the compound (±)-5-benzoyl-2,3-dihydro-1H-pyrrolizine-1-carboxylic acid with 2-amino-2-(hydroxymethyl)-1,3-propanediol (1:1) having the following structural formula (1)

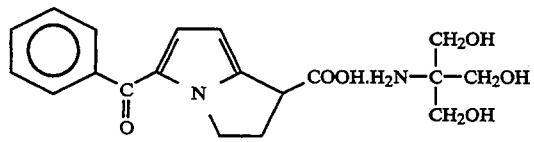

"Tobramycin" shall mean the antibiotic produced by *Streptomyces tinebrarius* also known as O-3-amino-3-deoxy-α-D-glucopyranosyl-(1→6)-O-[2,6-diamino-2,3,6-trideoxy-α-D-ribo-hexopyranosyl-(1→4)]-2-deoxy-D-streptamine. Tobramycin is represented by the following structural formula II:

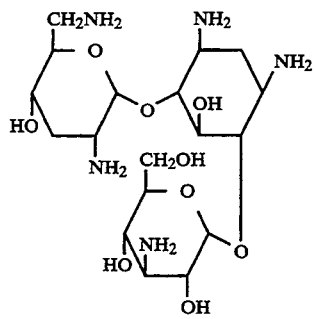

Tobramycin is a water soluble aminoglycosidic antibiotic having a broad spectrum of action against both gram negative and gram positive bacteria. Such aminoglycosidic antibiotics are useful in treating ocular infections and are used prophylactically before and after ocular surgery.

Formulations

The formulations of the present invention include an NSAID active agent in an effective amount for ophthalmic treatment, a quaternary ammonium preservative, a stabilizing amount of a nonionic polyoxyethylated octylphenol surfactant, optionally including other excipients such as a chelating agent, a tonicifier, a buffering system, a viscosity agent as well as other stabilizing agents.

In another embodiment of the invention, the formulation may also include an ophthalmologically acceptable antibiotic as a second active agent in an effective amount for ophthalmic treatment. The antibiotic is preferably tobramycin.

Ophthalmic solutions and suspensions typically contain an aqueous vehicle rather than an oily vehicle. Ophthalmic formulations must be sterile, and if intended for multiple dosing regimens, must be antimicrobially effective for their minimum reasonable shelf life, e.g., at least one year, and preferably two to three years or more. The ingredients used in the formulations of the present invention are typically commercially available or can be made by methods readily known to those skilled in the art.

Pharmaceutical ophthalmic formulations typically contain an effective amount, e.g., 0.001% to 10% wt/vol., most preferably 0.005% to 1% of an active ingredient (e.g., the NSAID of the present invention). The amount of active ingredient will vary with the particular formulation and the disease state for which it is intended. The total concentration of solutes should be such that, if possible, the resulting solution is isotonic with the lacrimal fluid (though this is not absolutely necessary) and has a pH in the range of 6–8.

The formulations of the present invention are prepared as solutions incorporating the above-described ingredients within the following approximate ranges:

| Ingredient | Amount |
| --- | --- |
| Active Agent* | 0.001% to 10.0% wt/vol.; |
| Preservative | 0.001% to 1.0% wt/vol.; |
| Surfactant | 0.001% to 1.0% wt/vol.; |
| Other Excipients | 0% to 10.0% wt/vol.; and |
| Purified Water | q.s. to 100%. |

*The active agent can be the NSAID alone or in combination with the antiobiotic.

Optional other excipients, such as a chelating agent and a tonicifier, are used in the following approximate proportions:

| Ingredient | Amount |
| --- | --- |
| Chelating agent | 0.01% to 1.0% wt/vol.; |
| Tonicifier | q.s. to achieve isotonicity with lacrimal fluid; and |
| 1N NAOH or 1N HCl | q.s. to adjust pH to 6.0 to 8.0 |

In a preferred ophthalmic NSAID solution, the ingredients are combined in the following proportions:

| Ingredient | Amount |
| --- | --- |
| NSAID | 0.50% wt/vol.; |
| BAC (50% aq. soln.) | 0.02% wt/vol.; |
| Octoxynol 40 (70% aq. soln.) | 0.01% wt/vol.; |
| EDTA Na$_2$ | 0.10% wt/vol.; |
| NaCl | q.s. for isotonicity with lacrimal fluid; |
| 1N NAOH or 1N HCl | q.s. to adjust pH to 7.4 ± 0.4; and |
| Purified Water | q.s. to 100%. |

This formulation may also include 0.30% wt/vol of an antibiotic such as tobramycin in addition to the NSAID. When the antibiotic is present the NaCl is replaced with a combination of NaCl, boric acid and Na borate.

The invention relates primarily to formulations having as the active agent ophthalmologically acceptable drugs (including the esters and pharmaceutically acceptable salts thereof) that can form a complex with a quaternary ammonium compound, particularly carboxyl group-containing NSAIDs.

NSAIDs useful in the practice of this invention include, for example, ketorolac (and the other compounds described as being ophthalmologically effective in U.S. Pat. No. 4,454,151 to Waterbury, issued Jun. 12, 1984, the pertinent portions of which are incorporated herein by reference), indomethacin, flurbiprofen sodium, and suprofen, including the esters and pharmaceutically acceptable salts thereof.

In place of, or in addition to, the NSAID may be another active ingredient in the form of an ophthalmologically acceptable antibiotic, preferably tobramycin. The antibiotic is present in an effective amount for ophthalmic treatment. The antibiotic tobramycin does not interfere with the corneal permeability of the NSAID.

Preservatives useful in the formulations of the present invention include quaternary ammonium compounds, such as cetyltrimethylammonium bromide, cetylpyridinium chloride and preferably, benzalkonium chloride.

The nonionic surfactants useful in the formulations of the present invention are preferably polyoxyethylated octylphenol surfactants including polyoxyethylene hydrogenated vegetable oils, such as polyethylene 60 hydrogenated castor oil, manufactured and sold by Kao Corp. of Japan under the trade name Emanon CH-60, and preferably ethoxylated octylphenol compounds, such as Octoxynol 10 and most preferably Octoxynol 40, manufactured and sold by GAF under the trade name Igepal CA897 (a 70% aqueous solution of Octoxynol 40). Octoxynol 40 is a nonionic polymeric surfactant material. More specifically, it is a nonionic polyoxyethylated octylphenol surfactant material sold commercially by GAF.

Among the optional excipients, the chelating agents useful in the formulations of the present invention include 8-hydroxyquinoline sulfate, citric acid, and preferably disodium edetate. Under certain conditions, the chelating agent may also enhance the anti-microbial effect due to its ability to render essential metal ions unavailable to the microbes.

Buffering systems optionally useful in the formulations of the present invention are based on, for example, citrate, borate, or phosphate.

Tonicifiers optionally useful in the formulations of the present invention include dextrose, potassium chloride and/or sodium chloride, preferably sodium chloride.

Viscosity agents optionally useful in the formulations of the present invention include the cellulose derivatives such as hydroxypropylmethyl cellulose, sodium carboxymethylcellulose, and hydroxyethylcellulose.

Other optional excipients useful in the formulations of the present invention include stabilizing agents such as antioxidants, e.g., sodium metabisulfate and ascorbic acid, depending on the NSAID used.

These formulations are prepared by dissolving the solutes (e.g., the NSAID, the preservative, the surfactant, the chelating agent, and the buffering agent) in a suitable quantity of water, adjusting the pH to about 6–8, preferably 6.8–8.0 and most preferably 7.4, making a final volume adjustment to 100% with additional water, and sterilizing the preparation using any suitable method known to those in the art.

Ophthalmic formulations incorporating the preservative system of the invention are physically stable (i.e., remain clear) and functionally stable (i.e., remain antimicrobially effective) for at least the minimum reasonable shelf life of such products. The inclusion of an antibiotic in the formulation does not effect the rate of diffusion of the NSAID.

Preferred Formulations

The preferred preservative system of the invention includes a quaternary ammonium preservative and a stabilizing amount of a nonionic surfactant.

The preferred ophthalmic formulation of the invention includes a NSAID active agent in an effective amount for ophthalmic treatment and an antimicrobially effective amount of the above-described preferred preservative system.

The preferred preservative of the invention is benzalkonium chloride.

The preferred surfactant of the invention is Octoxynol 40, especially when combined with benzalkonium chloride.

The preferred chelating agent of the invention is disodium edetate, especially when combined with benzalkonium chloride and Octoxynol 40.

The preferred antibiotic is one which does not interfere with the corneal permeability of the NSAID. Tobramycin is a preferred antiobiotic.

The preferred ophthalmic solutions of the invention include a NSAID, benzalkonium chloride, Octoxynol 40 and disodium edetate and may include, as a second active agent, tobramycin.

A preferred ophthalmic NSAID solution has the following formulation:

| Ingredient | Amount |
| --- | --- |
| NSAID | 0.50% wt/vol. |
| BAC (50% aq. soln.) | 0.02% wt/vol. |
| Octoxynol 40 (70% aq. soln.) | 0.01% wt/vol. |
| EDTA Na$_2$ | 0.10% wt/vol. |
| NaCl | q.s. for isotonicity with lacrimal fluid |
| 1N NAOH or 1N HCl | q.s. to adjust pH to 7.4 ± 0.4 |
| Purified Water | q.s. to 100% |

A preferred ophthalmic NSAID/antibiotic solution has the following formulation:

| Ingredient | Amount |
| --- | --- |
| NSAID | 0.50% wt/vol. |
| antibiotic | 0.30% wt/vol. |
| BAC (50% aq. soln.) | 0.02% wt/vol. |
| Octoxynol 40 (70% aq. soln.) | 0.01% wt/vol. |
| EDTA Na$_2$ (NaCl/boric acid/ Na borate | 0.10% wt/vol. q.s. for isotonicity with lacrimal fluid |
| 1N NAOH or 1N HCl | q.s. to adjust pH to 7.4 ± 0.4 |
| Purified Water | q.s. to 100% |

Most preferred is the ophthalmic solution according to the above formulations is wherein the NSAID is Ketorolac Tromethamine and when the antibiotic is present it is tobramycin.

Utility and Administration

This invention is directed to NSAID ophthalmic formulations and a method useful for treating ophthalmic diseases in mammals. These diseases are either caused by, associated with or accompanied by inflammatory processes, including, among others, glaucoma, cystoid macular edema, uveitis, diabetic retinopathy and conjunctivitis, or any trauma caused by eye surgery or eye injury.

The method of this invention is both curative and preventative. Where applied, for example, pre-surgically or immediately post-traumatically, i.e. before inflammation develops, it prevents development of inflammation. When applied directly to the eye suffering from any of the named ophthalmic diseases, it supresses already developed inflammatory processes.

When the formulation of the invention includes an antibiotic such as tobramycin, the formulation has antibacterial properties useful in eliminating and/or preventing a bacterial infection.

Ophthalmic formulations are typically administered by topical application to the eyelids or for instillation into the space (cul-de-sac) between the eyeball and the eyelids, by topically applied ophthalmic solutions, suspensions or ointments, or by subconjunctival injection.

The dosage level will, of course, depend on the concentration of the drops, the condition of the subject and the individual magnitude of responses to treatment. However, typical dosage ranges might be about 2–10 drops of solution of active ingredient per day wherein the solution includes 0.5 wt/vol. % of Ketorolac trimethamine and optionally 0.3 wt/vol. % of tobramycin.

For a more detailed discussion of ophthalmic formulations, their preparation and administration, see *Remington's Pharmaceutical Sciences*, 15th Ed., pages 1489–1504, (1975).

Testing

Ophthalmic formulations such as the solutions of the present invention are typically tested for physical stability, chemical stability, and preservative efficacy, both when they are first manufactured and after a fixed period of time (e.g., after two years). They are generally considered to be safe and clinically acceptable if proven to be well tolerated in the eye.

Physical stability is determined by observation of a solution after expiration of a fixed period of time. A solution is considered to be physically stable if its appearance (e.g., color and clarity) does not change and if the pH remains constant, within acceptable limits. Chemical stability involves a routine chemical analysis of the solution, to be sure that its active ingredient(s), preservatives and the excipients have not changed after a fixed period of time.

Preservative efficacy of the formulation prior to administration is tested by the procedure described in the U.S. Pharmacopia Compendiary, whereby a solution is challenged with a panel of microbes and a determination is made as to whether a given microbe survives in it.

EXAMPLES

The following examples are given to enable those skilled in the art to more clearly understand and to practice the present invention. They should not be considered as a limitation on the scope of the invention, but merely as being illustrative and representative thereof.

Example 1

This example illustrates the preparation of a representative pharmaceutical formulation for ophthalmic administration containing the NSAID Ketorolac Tromethamine.

| Ingredient | Amount |
| --- | --- |
| ketorolac tromethamine | 0.50% wt/vol. |
| BAC (50% aq. soln.) | 0.02% wt/vol. |
| Octoxynol 40 (70% aq. soln.) | 0.01% wt/vol. |
| EDTA Na$_2$ | 0.10% wt/vol. |
| NaCl | 0.79% wt/vol. |

The above ingredients are mixed, adding purified water until they are dissolved, the pH is adjusted to 7.4±0.4 and the balance of the formulation is made up with purified water, adding a quantity sufficient to make 100% volume. The solution is then sterilized.

Other NSAIDs, such as those described above, can be used as the active compound in the preparation of the formulation of this example.

Example 2

This example illustrates the preparation of a representative pharmaceutical formulation for ophthalmic administration containing the NSAID Ketorolac Tromethamine.

| Ingredient | Amount |
| --- | --- |
| ketorolac tromethamine | 0.50% wt/vol. |
| BAC (50% aq. soln.) | 0.01% wt/vol. |
| Octoxynol 40 (70% aq. soln.) | 0.02% wt/vol. |
| EDTA Na$_2$ | 0.20% wt/vol. |
| NaCl | 0.79% wt/vol. |

The above ingredients are mixed, adding purified water until they are dissolved, the pH is adjusted to 7.4±0.4 and the balance of the formulation is made up with purified water, adding a quantity sufficient to make 100% volume. The solution is then sterilized.

Other NSAIDs, such as those described above, can be used as the active compound in the preparation of the formulation of this example.

Example 3

This example illustrates the preparation of a representative pharmaceutical formulation for ophthalmic administration containing the NSAID Ketorolac Tromethamine and the antibiotic tobramycin.

| Ingredient | Amount |
| --- | --- |
| ketorolac tromethamine | 0.50% wt/vol. |
| tobramycin | 0.30% wt/vol. |
| BAC (50% aq. soln.) | 0.02% wt/vol. |
| Octoxynol 40 (70% aq. soln.) | 0.01% wt/vol. |
| EDTA Na$_2$ | 0.10% wt/vol. |
| NaCl | 0.18% wt/vol. |
| Boric Acid | 0.9% wt/vol. |
| Na Borate | 0.45% wt/vol. |

The above ingredients are mixed, adding purified water until they are dissolved, the pH is adjusted to 7.4±0.4 and the balance of the formulation is made up with purified water, adding a quantity sufficient to make 100% volume. The solution is then sterilized.

Other NSAIDs, such as those described above, can be used as the active compound in the preparation of the formulation of this example.

Example 4

This example illustrates the preparation of a representative pharmaceutical formulation for ophthalmic administration containing the antibiotic tobramycin.

| Ingredient | Amount |
| --- | --- |
| ketorolac tromethamine | 0.25% wt/vol. |
| tobramycin | 0.15% wt/vol. |
| BAC (50% aq. soln.) | 0.02% wt/vol. |
| Octoxynol 40 (70% aq. soln.) | 0.01% wt/vol. |
| EDTA Na$_2$ | 0.10% wt/vol. |
| NaCl | 0.79% wt/vol. |

The above ingredients are mixed, adding purified water until they are dissolved, the pH is adjusted to 7.4±0.4 and the balance of the formulation is made up with purified water, adding a quantity sufficient to make 100% volume. The solution is then sterilized.

Example 5

This example illustrates the preparation of a general pharmaceutical formulation for ophthalmic administration containing an NSAID and an antibiotic.

| Ingredient | Amount |
| --- | --- |
| NSAID | 0.50% wt/vol. |
| antibiotic | 0.3% wt/vol. |
| BAC (50% aq. soln.) | 0.01% wt/vol. |
| Octoxynol 40 (70% aq. soln.) | 0.02% wt/vol. |
| EDTA Na$_2$ | 0.20% wt/vol. |
| NaCl | 0.18% wt/vol. |
| Boric Acid | 0.9% wt/vol. |
| Na Borate | 0.45% wt/vol. |

Example 6

This example illustrates the preparation of a representative pharmaceutical formulation for ophthalmic administration containing the NSAID ketorolac tromethamine and tobramycin.

| Ingredient | Amount |
| --- | --- |
| ketorolac tromethamine | 0.50% wt/vol. |
| tobramycin | 0.30% wt/vol |
| BAC (50% aq. soln.) | 0.01% wt/vol. |
| Octoxynol 40 (70% aq. soln.) | 0.01% wt/vol. |
| EDTA Na$_2$ | 0.20% wt/vol. |
| NaCl | 0.18% wt/vol. |
| Boric Acid | 0.9% wt/vol. |

| Ingredient | Amount |
| --- | --- |
| Na Borate | 0.45% wt/vol. |

Other NSAIDs, such as those described above, can be used as the active compound in the preparation of the formulation of any of these examples.

Example 7

This example illustrates the preparation of a representative pharmaceutical formulation for ophthalmic administration containing the NSAID Ketorolac Tromethamine.

| Ingredient | Amount |
| --- | --- |
| ketorolac tromethamine | 0.50% wt/vol. |
| BAC (50% aq. soln.) | 0.01% wt/vol. |
| Octoxynol 40 (70% aq. soln.) | 0.02% wt/vol. |
| EDTA Na$_2$ | 0.20% wt/vol. |
| NaCl | 0.79% wt/vol. |

The above ingredients are mixed, adding purified water until they are dissolved, the pH is adjusted to 7.4±0.4 and the balance of the formulation is made up with purified water, adding a quantity sufficient to make 100% volume. The solution is then sterilized.

Other NSAIDs, such as those described above, can be used as the active compound in the preparation of the formulation of this example.

Example 8

This example illustrates the preparation of a representative pharmaceutical formulation for ophthalmic administration containing the NSAID ketorolac tromethamine.

| Ingredient | Amount |
| --- | --- |
| ketorolac tromethamine | 0.10% wt/vol. |
| BAC (50% aq. soln.) | 0.004% wt/vol. |
| Octoxynol 40 (70% aq. soln.) | 0.004% wt/vol. |
| EDTA Na$_2$ | 0.05% wt/vol. |
| NaCl | 0.88% wt/vol. |

The above ingredients are mixed, adding purified water until they are dissolved, the pH is adjusted to 7.4±0.4 and the balance of the formulation is made up with purified water, adding a quantity sufficient to make 100% volume. The solution is then sterilized.

Other NSAIDs, such as those described above, can be used as the active compound in the preparation of the formulation of this example.

Example 9

This example illustrates the preparation of a representative pharmaceutical formulation for ophthalmic administration containing the NSAID flurbiprofen sodium.

| Ingredient | Amount |
| --- | --- |
| Flurbiprofen Sodium | 0.03% wt/vol. |
| BAC (50% aq. soln.) | 0.02% wt/vol. |
| Octoxynol 40 (70% aq. soln.) | 0.01% wt/vol. |
| EDTA Na$_2$ | 0.10% wt/vol. |
| NaCl | 0.90% wt/vol. |

The above ingredients are mixed, adding purified water until they are dissolved, the pH is adjusted to 7.4±0.4 and the balance of the formulation is made up with purified water, adding a quantity sufficient to make 100% volume. The solution is then sterilized.

Other ophthalmic drugs and NSAIDs, such as those described above, can be used as the active compound in the preparation of the formulation of this example.

Use and Administration

Physical stability of the formulations of the present invention is measured by preparing clear formulations, e.g., according to the foregoing Examples, sealing them in sterilized containers, and observing the clarity of the solution after a period of one month and again after five months. Solutions that remain clear are considered stable in this procedure.

The formulations of the present invention have proven to be stable when tested in accordance with the above procedure. Formulations using surfactants other than the nonionic surfactants of the invention did not remain clear and were not stable.

Preservative efficacy of the formulations of the present invention is measured by preparing formulations, e.g., according to the foregoing Examples, and subjecting them to the U.S. Pharmacopia antimicrobial challenge.

The formulations of the present invention demonstrate preservative efficacy when tested in accordance with the above procedure.

Formulations of the present invention are freely flowable liquids which can be administered directly to the eye using a conventional means such as eyedroppers. The amount of active ingredient administered will vary with the individual and/or the type of disease or condition being treated. The NSAID's such as ketorolac and antibiotics such as tobramycin are generally administered in an amount of about 1-2 drops per eye with drops containing about 25 microliters of formulation. The drops are generally administered 3 to 4 times per day.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. An ophthalmologically acceptable ketorolac formulation, comprising:
   ketorolac in an effective amount for ophthalmic treatment between 0.001% and 10.0% wt/vol;
   an ophthalmologically acceptable antibiotic in an effective amount for ophthalmic treatment between 0.001% and 10.0% wt/vol;

a quaternary ammonium preservative in an amount between 0.001% and 1.0% wt/vol;

octoxynol 40 in a stabilizing amount between 0.001% and 1.0% wt/vol; and an aqueous vehicle q.s. to 100%.

2. The formulation of claim 1 wherein said quaternary ammonium preservative is benzalkonium chloride.

3. The formulation of claim 2 wherein said antibiotic is tobramycin.

4. The formulation of claim 3, further comprising:

a chelating agent in an amount between 0.01% and 1.0% wt/vol;

a tonicifier q.s. to achieve isotonicity with lacrimal fluid; and

1N NaOH or 1N HCl q.s. to adjust pH to 7.4±0.4.

5. The formulation of claim 4, comprising:

| | |
|---|---|
| ketorolac tromethamine | 0.50% wt/vol; |
| tobramycin | 0.30% wt/vol; |
| benzalkonium chloride (50% aqueous solution) | 0.02% wt/vol; |
| octoxynol 40 (70% aqueous solution) | 0.01% wt/vol; |
| Na$_2$EDTA | 0.10% wt/vol; |
| NaCl | 0.18% wt/vol; |
| boric acid | 0.9% wt/vol; |
| Na borate | 0.45% wt/vol; |
| 1N NAOH or 1N HCl | q.s. to pH 7.4 ± 0.4; and |
| purified water | q.s. to 100%. |

6. A method of treating ophthalmic disease, comprising administering to a mammal suffering therefrom a ketorolac formulation comprising:

ketorolac in an effective amount for ophthalmic treatment between 0.001% and 10.0% wt/vol;

an ophthalmologically acceptable antibiotic in an effective amount for ophthalmic treatment between 0.001% and 10.0% wt/vol;

a quaternary ammonium preservative in an amount between 0.001% and 1.0% wt/vol octoxynol 40 in a stabilizing amount between 0.001% and 1.0% wt/vol; and an aqueous vehicle q.s. to 100%.

7. The method of claim 6 wherein said quaternary ammonium preservative is benzalkonium chloride.

8. The method of claim 7 wherein said antibiotic is tobramycin.

9. The method of claim 8, further comprising:

a chelating agent in an amount between 0.01% and 1.0% wt/vol;

a tonicifier q.s. to achieve isotonicity with lacrimal fluid; and

1N NaOH or 1N HCl q.s. to adjust pH to 7.4±0.4.

10. The method of claim 9, comprising:

| | |
|---|---|
| ketorolac tromethamine | 0.50% wt/vol; |
| tobramycin | 0.30% wt/vol; |
| benzalkonium chloride (50% aqueous solution) | 0.02% wt/vol; |
| octoxynol 40 (70% aqueous solution) | 0.01% wt/vol; |
| Na$_2$EDTA | 0.10% wt/vol; |
| NaCl | 0.18% wt/vol; |
| boric acid | 0.9% wt/vol; |
| Na borate | 0.45% wt/vol; |
| 1N NAOH or 1N HCl | q.s. to pH 7.4 ± 0.4; and |
| purified water | q.s. to 100%. |

* * * * *